(12) United States Patent
Van Der Walt et al.

(10) Patent No.: US 7,252,744 B2
(45) Date of Patent: Aug. 7, 2007

(54) TREATMENT OF FLUOROCARBON FEEDSTOCKS

(75) Inventors: Izak Jacobus Van Der Walt, Krugersdorp (ZA); Klaus Hintzer, Kastl (DE); Gernot Löhr, Burgkirchen (DE)

(73) Assignees: South African Nuclear Energy Corporation Limited, District Brits (ZA); 3M Innovative Properties Company, St. Paul, MN (US)

( * ) Notice: Subject to any disclaimer, the term of this patent is extended or adjusted under 35 U.S.C. 154(b) by 496 days.

(21) Appl. No.: 10/203,527

(22) PCT Filed: Feb. 9, 2001

(86) PCT No.: PCT/IB01/00156

§ 371 (c)(1),
(2), (4) Date: Nov. 20, 2002

(87) PCT Pub. No.: WO01/58840

PCT Pub. Date: Aug. 16, 2001

(65) Prior Publication Data

US 2003/0114600 A1    Jun. 19, 2003

(30) Foreign Application Priority Data

Feb. 10, 2000    (ZA) .............................. 2000/0637

(51) Int. Cl.
*B01J 19/08*    (2006.01)
(52) U.S. Cl. ................... 204/169; 219/121.37
(58) Field of Classification Search ........... 422/186.22; 204/165, 169; 165/94; 219/121.37
See application file for complete search history.

(56) References Cited

U.S. PATENT DOCUMENTS

| 3,555,823 | A |   | 1/1971 | Guman ...................... 60/202 |
| 3,622,493 | A | * | 11/1971 | Crusco .................. 422/186.23 |
| 4,606,760 | A |   | 8/1986 | Fritz et al. ................. 75/10.19 |
| 5,008,511 | A | * | 4/1991 | Ross ..................... 219/121.48 |
| 5,399,833 | A |   | 3/1995 | Camacho ............... 219/121.59 |
| 5,611,896 | A | * | 3/1997 | Swanepoel et al. ......... 204/169 |

(Continued)

FOREIGN PATENT DOCUMENTS

EP    0039517    11/1981

(Continued)

OTHER PUBLICATIONS

Patent Abstracts of Japan Publication No. 03004933 dated Jan. 10, 1991.

(Continued)

*Primary Examiner*—Kishor Mayekar
(74) *Attorney, Agent, or Firm*—Ladas & Parry LLP

(57) ABSTRACT

A method of treating a fluorocarbon feedstock includes generating, in a high temperature zone, an electrical arc between at least one cathode and at least one anode, generating in the high temperature zone and by means of the electrical arc and a plasma gas, an upwardly burning thermal plasma having a tail flame, allowing a solid particulate fluorocarbon feedstock comprising at least on fluorocarbon compound to form a reactive thermal mixture with the thermal plasma tail flame, with the fluorocarbon compound dissociating into at least one fluorocarbon precursor or reactive species, and cooling the reactive thermal mixture to form, from the fluorocarbon precursor of reactive species, at least one more desirable fluorocarbon compound.

19 Claims, 2 Drawing Sheets

U.S. PATENT DOCUMENTS

2004/0094399 A1* 5/2004 Van Der Walt et al. .... 204/156

FOREIGN PATENT DOCUMENTS

| EP | 0093632 | 11/1983 |
| EP | 0282827 | 9/1988 |
| GB | 766324 | 1/1957 |
| GB | 2066227 | 7/1981 |
| GB | 2066227 A * | 7/1981 |
| JP | 34933 | 1/1991 |

OTHER PUBLICATIONS

Derwent Abstract No. 95-105138 RU 2 017 037 dated Jul. 30, 1994.

* cited by examiner

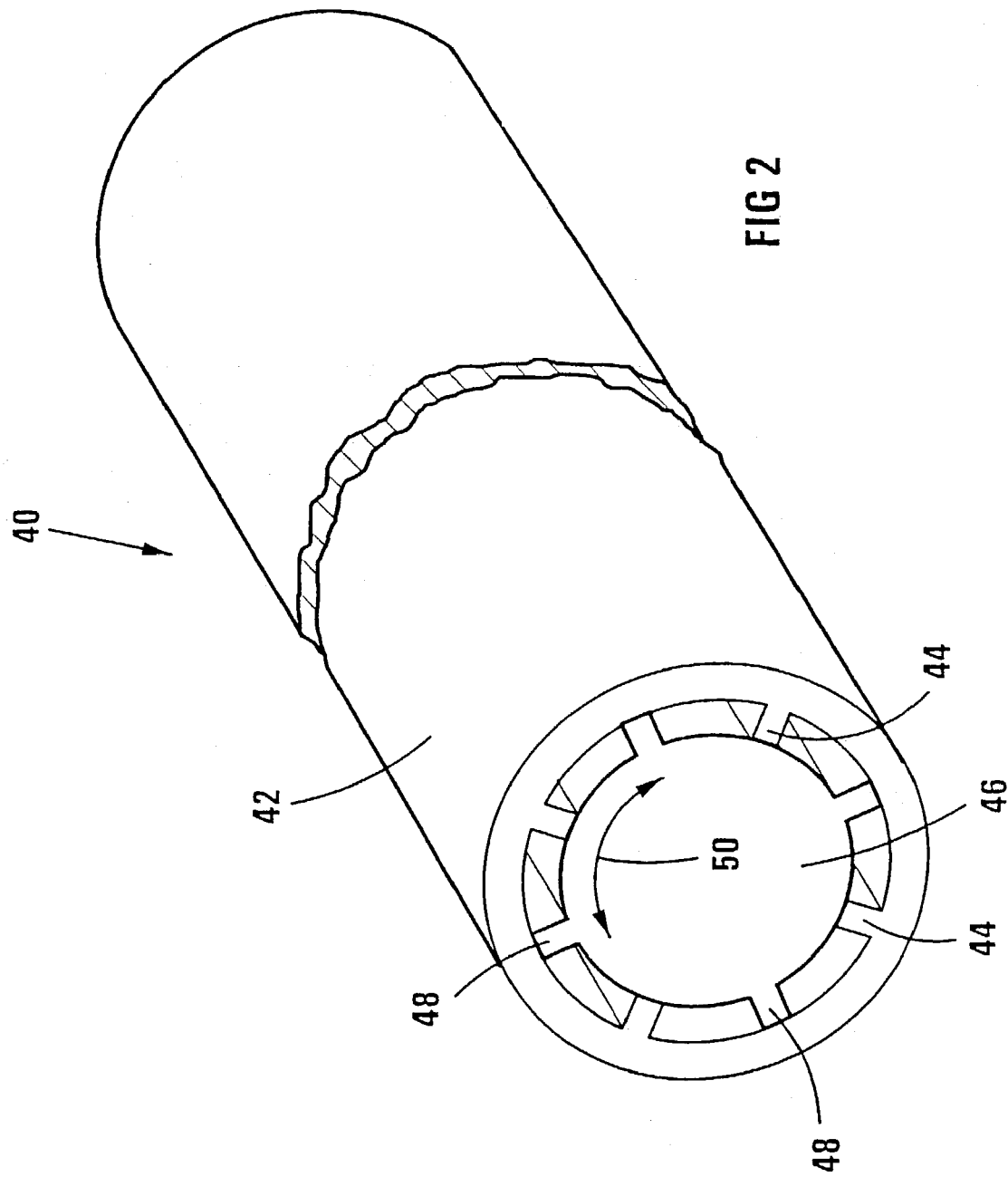

TREATMENT OF FLUOROCARBON FEEDSTOCKS

This application is the U.S. National Phase of International Application No. PCT/IB01/00156 filed on Feb. 9, 2001.

THIS INVENTION relates to the treatment of fluorocarbon feedstocks. It relates in particular to a method of treating a fluorocarbon feedstock, to an installation for treating a fluorocarbon feedstock, and to a quench probe for use in the method and in the installation.

According to a first aspect of the invention, there is provided a method of treating a fluorocarbon feedstock, which method includes generating, in a high temperature zone, an electrical arc between at least one cathode and at least one anode;

generating in the high temperature zone and by means of the electrical arc and a plasma gas, an upwardly burning thermal plasma having a tail flame;

allowing a solid particulate fluorocarbon feedstock comprising at least one fluorocarbon compound to form a reactive thermal mixture with the thermal plasma tail flame, with the fluorocarbon compound dissociating into at least one fluorocarbon precursor or reactive species; and cooling the reactive thermal mixture to form, from the fluorocarbon precursor or reactive species, at least one more desirable fluorocarbon compound.

The plasma gas may, in one embodiment of the invention, be an inert gas such as argon, nitrogen, helium, or mixtures thereof. The inert gas thus serves only as a heat source and to sustain the plasma, and does not react with the fluorocarbon precursor or reactive species. However, in another embodiment of the invention, the plasma gas may be a reactive gas such as tetrafluoromethane ($CF_4$) which will thus, in the thermal plasma and hence in the reactive thermal mixture, dissociate into fluorine containing species and carbon containing species, which, on cooling of the reactive thermal mixture, will react with the fluorocarbon precursor or reactive species to form said at least one more desired fluorocarbon compound. In yet another embodiment of the invention, the plasma gas may comprise a mixture of the inert gas and the reactive gas as hereinbefore described.

The feedstock may, in particular, be a filled or an unfilled material, which is not directly usable, such as polytetrafluoroethylene ('PTFE'), tetrafluoroethylene hexafluoropropylene vinylidenefluoride ('THV'), fluorinated ethylene-propylene copolymer ('FEP'), perfluoroalkoxy copolymer ('PFA'), or the like. By 'filled' is meant that the fluorocarbon feedstock may contain elements or substances such as silica, copper, carbon, etc which were originally added to fluorocarbon material to impart specific properties thereto. Once such material has been used and thus has become not directly usable, but suitable for use as the feedstock in the method of the invention, it will still contain these elements. In the method of the invention, these materials are depolymerized, and the more desirable fluorocarbon compound, or a mix of such compounds, formed therefrom.

If desired or necessary, the solid particulate feedstock may be pretreated to remove surface contaminants such as oil and dirt, eg by means of solvent extraction.

Typical products which may be obtained are tetrafluoromethane ($CF_4$), tetrafluoroethylene ($C_2F_4$), hexafluoroethane ($C_2F_6$), hexafluoropropylene ($C_3F_6$), hexafluorobutylene ($C_4F_6$), cyclic octafluorobutane (c-$C_4F_8$), decafluorobutane ($C_4F_{10}$), octafluoropropane ($C_3F_8$) and other $C_xF_y$ chains where x and y are integers.

The cathode and anode, ie the electrodes, may thus be those of a plasma torch or plasmatron driven by a power supply. The high temperature zone may be the region in and around, and in the immediate vicinity of, the arc of the plasma torch or plasmatron, ie the arc between the electrodes.

In principle, any suitable plasmatron or torch may be used. For example, the plasmatron may comprise a single water cooled hot cathode and a battery of up to three water cooled anodes, with the arc thus passing between the cathode and anodes. The cathode may include a suitable insert such as a tungsten or graphite insert.

The feedstock may be introduced into the plasma tail flame which forms at the outlet of the plasmatron or torch. The plasma gas may be fed separately into the high temperature zone through the torch or plasmatron, ie into the torch between the electrodes.

The generation of the thermal plasma, the dissociation of the fluorocarbon compound, and the cooling of the reactive thermal mixture may thus be effected in a plasma reactor. The reactor, which may be lined, eg with graphite, will thus include a reaction chamber in which the thermal plasma tail flame is expanded, the fluorocarbon compound is dissociated, and the reactive thermal mixture is cooled, with the thermal plasma tail flame expansion and the fluorocarbon compound dissociation being effected in a first zone of the reaction chamber, and the reactive thermal mixture cooling being effected in a second zone of the reaction chamber. The plasmatron will thus be mounted to the reactor adjacent the first zone of the reaction chamber so that the plasma generation and the tail flame expansion can be effected in the first zone of the reaction chamber. The reaction chamber may be of inverted conical shape, with the torch or plasmatron located at the bottom of the reaction chamber.

The cooling of the second zone of the reaction chamber may be effected by means of a quench probe, which may be a self-cleaning quench probe. The self-cleaning quench probe may comprise an outer cylindrical component mounted to the reactor, providing a central passageway and adapted to cool the hot gas or reactive thermal mixture passing through the passageway; a plurality of circumferentially spaced elongate teeth or scrapers protruding inwardly from the outer component into the passageway; an inner cylindrical component located with clearance inside the outer component, with the inner component also adapted to cool the hot gas or reactive thermal mixture passing along the peripheral gap between the components; a plurality of circumferentially spaced elongate teeth or scrapers protruding outwardly from the inner component into the passageway, with these teeth or scrapers being staggered with respect to the teeth or scrapers on the outer component; and drive means for driving the one cylindrical component to oscillate relative to the other cylindrical component. The drive means may, for example, comprise a spring loaded piston driven arm.

Instead, however, any other suitable quenching means can be used such as rapid expansion of the product gas, gas quenching by means of another gas which is cold, or the like.

The reactor installation comprising the plasmatron, the reactor and the quench probe may thus be a so-called spouted bed reactor installation in which the plasmatron is located at the bottom of the reaction chamber and arranged such that the thermal plasma which forms burns upwardly, and in which the quench probe protrudes into the upper end portion of the reaction chamber, directly above the plasmatron. While the quench probe will normally be located vertically, it may also be located at different angles to the vertical, depending on the product required, the process parameters, etc. The reaction chamber may, in particular, be of inverted conical shape, as hereinbefore described.

The feeding of the plasma gas into the high temperature zone may be effected by injecting the gas into the torch between the electrodes in such a manner that the gas flow forms a vortex stabilized thermal plasma in the reaction zone of the reactor. Additionally, plasma gas may be introduced between consecutive anodes, to enhance and sustain the vortex into the expansion area of the reaction chamber.

The tail flame may be directed vertically upwardly, with the quench probe extending vertically, or at an angle, as hereinbefore described.

While the solid particulate feedstock may, in principle, be introduced into the cavity or the first zone of the reaction chamber in any desired manner, gravity feed may, in particular, be employed since relatively large feedstock particles can readily be used, eg particles in the size range 1 to 20 mm, preferably from 8 to 15 mm. Thus, the feedstock may be fed vertically into the chamber under gravity, immediately above the torch.

The feeding of the feedstock into the reactor may be effected in a batch fashion, in a semi-continuous fashion, or in a continuous fashion. By 'batch' is meant that a predetermined quantity of the fluorocarbon is loaded into the reactor and allowed to react to completion with the hot plasma gas. By 'semi-continuous' is meant that a hopper is filled with feedstock, with this feedstock then being fed into the reactor at a continuous, normally constant, feed rate until the hopper is empty, whereafter the hopper may be refilled. By 'continuous' is meant that the feedstock is fed continuously into the reactor, normally at a more-or-less constant feed rate. It is believed that a continuous feed operation can beneficially be used with feedstocks having relatively high evaporation rates. Typically, such feedstocks have boiling points of less than 1000° C.

The reaction chamber may be operated under pressures ranging from near vacuum to elevated pressures, depending on the specific reaction, ie depending on the feedstock and the desired fluorocarbon compound to be formed. Evacuation may be effected through the quench probe.

Normally a spread of fluorocarbon compounds will form as products. The method may then include separating the various products from one another.

According to a second aspect of the invention, there is provided an installation for treating a fluorocarbon feedstock, which installation comprises a reactor having an upwardly outwardly flaring reaction chamber;

plasma generating means at the bottom of the reaction chamber; and quench means in the reaction chamber above the plasma generating means, for quenching or cooling a reactive thermal mixture which, in use, forms in the reaction chamber.

The reaction chamber may, in particular, be of inverted conical form, with the plasma generating means located at the apex of the reaction chamber and the quench means being located directly above the plasma generating means, in an upper portion or zone of the reaction chamber.

The reactor may be lined, eg with graphite, as hereinbefore described, and may be provided with an inlet for feeding a feedstock into the reaction chamber, and an outlet for withdrawing product from the reaction chamber.

The plasma generating means may include a cathode and an anode as hereinbefore described, and may thus be a plasma torch or plasmatron as hereinbefore described.

The quench means may be an elongate quench probe as hereinbefore described, located in the reactor outlet. The quench probe may be located vertically.

According to a third aspect of the invention, there is provided a quench probe which comprises an outer cylindrical component providing a central passageway and adapted to cool a hot gas passing through the passageway;

a plurality of circumferentially spaced elongate teeth or scrapers protruding inwardly from the outer component into the passageway;

an inner cylindrical component located with clearance inside the outer component, with the inner component adapted to cool the hot gas passing along the peripheral gap between the components;

a plurality of circumferentially spaced elongate teeth or scrapers protruding outwardly from the inner component into the passageway, with these teeth or scrapers being staggered with respect to the teeth or scrapers on the outer component; and drive means for driving the one component to oscillate relative to the other component.

The inner component may be located centrally or concentrically within the outer component. The same number of teeth or scrapers may be provided on the inner and outer components. The teeth or scrapers may be spaced equidistantly apart on their components. The teeth or scrapers may extend parallel to one another.

The components may be hollow and/or may be provided with passages to permit a cooling fluid, such as water, to pass through them in order to cool or quench the hot gas.

The drive means may, as also hereinbefore described, comprise a spring loaded piston driven arm attached to one of the cylindrical components.

Due to the oscillation of the one component relative to the other, removal of solidified or sublimated material deposited on the surfaces thereof, on passage of the gas through the annular gap between the components, is achieved.

The quench probe is particularly suited for use in a plasma reactor as hereinbefore described; however, it is not limited only to such use. Normally, the outer component will be fixed to the reactor, with the inner component oscillating relative to the outer component.

The invention will now be described by way of example, with reference to the accompanying diagrammatic drawings.

In the drawings,

FIG. 2 shows a three-dimensional view of the quench probe of the reactor of FIG. 1.

Figure 1:
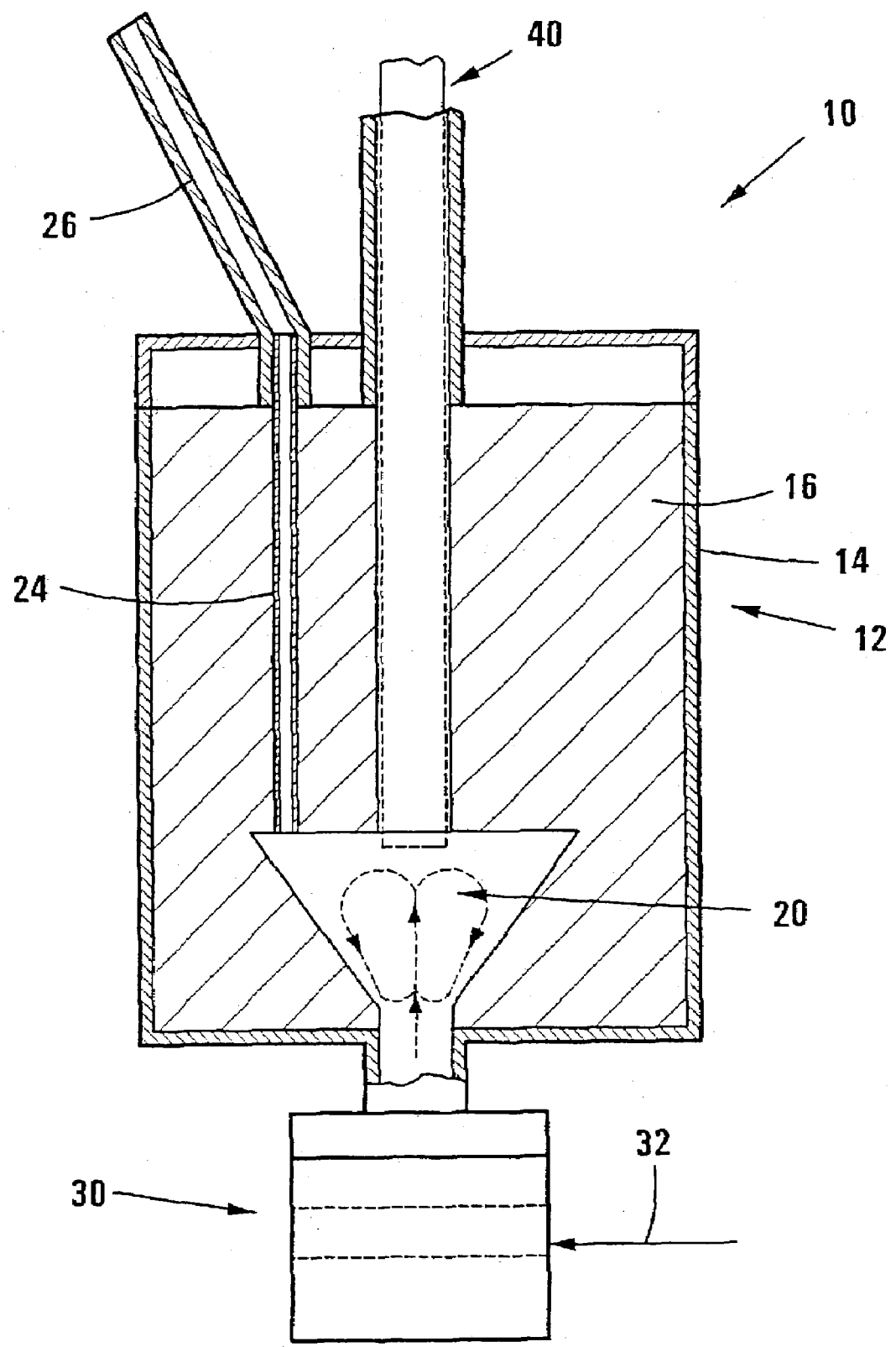
FIG. 1 shows, in simplified flow diagram form, an installation for carrying out a method of treating a fluorocarbon feedstock, in accordance with the invention.

In the drawings, reference numeral 10 generally indicates an installation for carrying out a method of treating a fluorocarbon feedstock, according to the invention.

The installation 10 includes a reactor, generally indicated by reference numeral 12. The reactor 12 comprises a shell 14 internally lined with graphite 16. A reaction chamber, generally indicated by reference numeral 20, is provided inside the reactor 12. The reaction chamber 20 is of inverted conical shape. A vertically extending feed conduit 24 leads into the cavity 20, with a feed conduit 26 attached to the conduit 24.

The installation 10 includes a plasma torch or plasmatron, generally indicated by reference numeral 30. The plasma torch or plasmatron 30 comprises a water cooled hot cathode (not shown) and a battery of up to three water cooled anodes (not shown). The hot cathode includes a tungsten insert (not shown). A plasma gas injection flow line 32 leads into the plasma torch 30. In use, plasma gas is injected into the torch through the flow line 32 between the cathode and anodes in such a manner that the resultant gas stream forms a vortex stabilized plasma and also has an upwardly directed tail flame.

The installation 10 also includes a self-cleaning quench probe, generally indicated by reference numeral 40, protruding into the lower end of the reactor 12. The self-cleaning quench probe 40 comprises an elongate watercooled cylindrical outer component 42, which is fixed to the reactor 12. The outer component 42 thus has a central passageway into which protrudes equally spaced elongate radially inwardly protruding teeth or scrapers 44. Inside the passageway of the outer component 42 is located, with peripheral clearance, an elongate watercooled cylindrical inner component 46. Equally spaced elongate radially outwardly protruding teeth or scrapers 48 are provided on the inner component 46, with the teeth 48 being spaced circumferentially from the teeth 44. The teeth 44, 48 may extend the full length of the components 42, 46, and the components 42, 46 are of substantially the same length. The inner component 46 is provided with drive means (not shown), such as a spring loaded piston driven arm, for driving it to oscillate relative to the outer component 42 as indicated by the arrow 50. Removal of solid contaminants from the components 42, 46 is thus achieved by means of the oscillating teeth 44, 48. By moving the quench probe 40 up and down, the effective length of the reaction chamber can be increased or decreased, thereby to optimize the reaction chamber length.

The quench probe 40 is thus a double annular water cooled probe designed to cool the plasma gas or reactive thermal mixture that forms inside the reaction chamber 20 as hereinafter described, down to below 200° C. at a rate of about $10^5$° C./second. The probe is self cleaning to prevent blockages thereof since solidified or sublimated material forms on the surfaces of the probe in use.

A flow line (not shown) leads from the upper end of the quench probe 40 to a filter (not shown), with a flow line (not shown) leading from the filter to a vacuum pump (not shown). A product withdrawal line (not shown) leads from the pump discharge. By means of the vacuum pump, a vacuum is thus drawn on the reaction chamber 20.

In use, on feeding a plasma gas, such as argon, into the plasma torch 30 through the flow line 32, a plasma is generated between the cathode and anodes. The plasma burns upwardly, and an upwardly moving plasma tail flame is formed in the reaction chamber 20. Feedstock is gravity fed through the conduits 26, 24 into the reaction chamber 20. Since the reaction chamber 20 is in the shape of an inverted cone, the feedstock particles swirl around continuously and vigorously, and always recycle back into the plasma tail flame. Thus, as the plasma burns upwardly into the reaction chamber 20, the feedstock particles swirl around, as indicated in broken line in FIG. 1, and are confined within the plasma tail flame, ie contact with the plasma is maximized. This forces the entire feedstock to be converted, while the off gases, including the desired product compound, are quenched at the top of the reaction chamber, evacuated and quenched through the quench probe 40. When unfilled polymeric material is used as feedstock, the polymeric compounds rapidly evaporate and depolymerize into their monomeric constituents. Filled polymeric material can also be used as feedstock provided the filler is relatively inert at the working temperature in the reactor or does not partake detrimentally in the reactions of the fluorocarbon precursors or species. In some applications, the graphite lining 16 can also partake in the reaction, particularly when the feedstock contains carbon material and a $CF_4$ plasma is used.

In the specific examples hereinafter discussed, a 30 kW plasma torch or plasmatron was used. A plasma gas flow rate of about 3 kg/hour was used. Before commencing the tests or examples, the system was evacuated to about 10 kPa, and flushed with argon. The plasma was initiated by a high voltage starter (not shown) and maintained by a 30 kW power supply. After the argon plasma initiation had been completed, a switch-over to the desired plasma gas was done. It will, however, be appreciated that on other reactor systems, the plasmatron can be initiated directly on the desired plasma gas, depending on the design of the plasmatron.

EXAMPLE 1

The installation 10, operating with an argon plasma, was used. The feedstock was solid particulate THV. After 70 minutes, a blockage was experienced. It was found that the reactor was covered in a soft blanket of brittle carbon layers up to 7 mm thick. This test was done on a semi-continuous basis.

EXAMPLE 2

The same installation as in Example 1, was used. Thus, this Example was also conducted on a semi-continuous basis, and the same feedstock was used. In this case, the feedstock was converted using a $CF_4$ plasma under the same conditions as in Example 1. The $CF_4$ plasma gave a very hard thin layer of carbon after 90 minutes. Almost no blockage occurred.

The results obtained are set out in Tables 1 and 2.

TABLE 1

Results

|  | Example 1 Ar plasma gas | Example 2 $CF_4$ plasma gas |
| --- | --- | --- |
| Torch efficiency (%) | 24.32 | 63.85 |
| Energy In (kW) | 6.6 | 25.8 |
| Energy Out (kW) | 7.3 | 27 |
| Enthalpy below torch (kWh/kg) | 0.64 | 5.18 |
| Run time (min) | 70 | 90 |
| Particulate fluorocarbon feed rate (kg/h) | 0.7 | 0.55 |
| Mass feedstock fed (kg) | 0.7 | 0.8 |
| Mass deposit relative to feed (kg/kg) | 0.0927 | 0.0712 |

The torch efficiency for the Ar plasma was lower than for the $CF_4$ plasma. The reason for this is that an Ar torch for a spouted bed reactor has, it is believed, not yet been optimized; additionally, a $CF_4$ torch was used for the Ar plasma run. From Table 1, it can be seen that the mass of the deposit in the Ar run is slightly higher than in the $CF_4$ run.

There was a substantial difference in the nature of the carbon deposits in Examples 1 and 2. It appears that most of the carbon from the Ar run (Example 1) did not enter the gas phase. On the other hand, the carbon that deposited from the $CF_4$ run (Example 2) did enter the gas phase. The $CF_4$ plasma is hotter than the Ar plasma, and this is advantageous for the conversion mechanism. For the spouted bed reactor used in these preliminary examples, it was found to be more advantageous to use $CF_4$ since, when using the cooler argon plasma, the reactor blocked very quickly as a result of excessive carbon deposits on all the cold surfaces, including the quench probe and carbon filter, even though the TFE yield ($C_2F_4$) was greater with the Ar-plasma (Example 1, Table 2).

TABLE 2

Analytical Results

| Plasma products | Example 1 Ar plasma gas | Example 1* | Example 2 $CF_4$ plasma gas |
| --- | --- | --- | --- |
| Air/Ar (%) | 90 | — | — |
| $CF_4$ (%) | 0.4 | 4 | 29.1 |

TABLE 2-continued

Analytical Results

| Plasma products | Example 1<br>Ar plasma gas | Example 1* | Example 2<br>$CF_4$ plasma gas |
|---|---|---|---|
| $C_2F_6$ (%) | 1.8 | 18 | 21.4 |
| $C_2F_4$ (%) | 6.2 | 62 | 26.9 |
| $C_3F_8$ (%) | 0.2 | 2 | 4.7 |
| $C_3F_6$ (%) | 0.4 | 4 | 4.2 |
| Other | 1 | 10 | 13.7 |

*The same as Example 1 but normalized for Ar, in order to compare with the $CF_4$ run of Example 2

It is believed that the method of the present invention is suitable for converting, in particular, not directly usable solid materials into usable high value products at a relatively low cost.

The invention claimed is:

1. A method of treating a solid particulate fluoropolymer, which method includes
generating, in a high temperature zone, an electrical arc between at least one cathode and at least one anode;
generating in the high temperature zone and by means of the electrical arc and a plasma gas, an upwardly burning thermal plasma having an expanded tail flame;
introducing a solid particulate fluoropolymer having particles in a size range of 1 mm to about 20 mm into the expanded tail flame for forming a reactive thermal mixture with the expanded tail flame and in which the particles are confined within the tail flame so that they swirl around continuously in the tail flame, disassociating the fluoropolymer into at least one fluorocarbon precursor or reactive species; and
quenching a gas phase comprising the fluorocarbon precursor or reactive species to form at least one monomeric fluorocarbon compound.

2. A method according to claim 1, wherein the solid particulate fluoropolymer is a perfluorinated polymer.

3. A method according to claim 2, wherein the solid particulate fluoropolymer is a filled material.

4. A method according to claim 2, wherein the solid particulate fluoropolymer is a not-directly-usable material.

5. A method according to claim 1, wherein the solid particulate fluoropolymer is a partially fluorinated polymer.

6. A method according to claim 1, wherein the monomeric fluorocarbon compound that is formed comprises tetrafluoroethylene.

7. A method according to claim 1, wherein the plasma gas is an inert gas which acts only as a heat source and to sustain the plasma, and does not react with the fluorocarbon precursor or reactive species.

8. A method according to claim 1, wherein the plasma gas is a reactive gas which, in the thermal plasma and hence in the reactive thermal mixture, dissociates into fluorine containing species and carbon containing species, which, on the quenching of the gas phase, react with the fluorocarbon precursor or reactive species to form the monomeric fluorocarbon compound.

9. A method according to claim 1, wherein the plasma gas comprises a mixture of an inert gas and a reactive gas.

10. A method according to claim 1, wherein the cathode and the anode are electrodes of a plasma torch or plasmatron driven by a power supply, with the high temperature zone being a region in and around, and in the immediate vicinity of, the arc between the electrodes.

11. A method according to claim 10, wherein the plasma gas being is fed separately into the high temperature zone between the electrodes of the torch or plasmatron.

12. A method according to claim 11, wherein the solid particulate fluoropolymer is fed vertically and under gravity into the plasma tail flame, immediately above the plasmatron or torch.

13. A method according to claim 11, wherein the generation of the thermal plasma, the dissociation of the fluoropolymer, and the quenching of the gas phase are effected in a plasma reactor which includes a reaction chamber in which the thermal plasma tail flame is expanded, the fluoropolymer is dissociated, and the gas phase is quenched, with the thermal plasma tail flame expansion and the fluoropolymer dissociation being effected in a first zone of the reaction chamber, and the gas phase quenching being effected in a second zone of the reaction chamber, and with the torch or plasmatron being mounted to the reactor adjacent the first zone of the reaction chamber.

14. A method according to claim 13, wherein the reaction chamber is of inverted Conical shape, with the torch or plasmatron located at the bottom of the reaction chamber.

15. A method according to claim 13, wherein the cooling of the second zone of the reaction chamber is effected by means of a self-cleaning quench probe.

16. A method according to claim 15, wherein the self-cleaning quench probe comprises
an outer cylindrical component mounted to the reactor, the outer cylindrical component providing a central passageway and adapted to cool the hot gas phase passing through the passageway;
a plurality of circumferentially spaced elongate teeth or scrapers protruding inwardly from the outer component into the passageway;
an inner cylindrical component located with clearance inside the outer component, with the inner component also adapted to cool the hot gas phase passing along the peripheral gap between the components;
a plurality of circumferentially spaced elongate teeth or scrapers protruding outwardly from the inner component into the passageway, with these teeth or scrapers being staggered with respect to the teeth or scrapers on the outer component; and
drive means for driving the one cylindrical component to oscillate relative to the other cylindrical component.

17. A method according to claim 15, wherein the plasmatron, the reactor and the quench probe are part of a spouted bed reactor installation in which the plasmatron is located at the bottom of the reaction chamber and arranged such that the thermal plasma which forms burns upwardly, and in which the quench probe protrudes into the upper end portion of the reaction chamber, directly above the plasmatron.

18. A method according to claim 15, wherein the feeding of the plasma gas into the high temperature zone is effected by injecting the plasma gas into the torch between the electrodes in such a maimer that the gas flow forms a vortex stabilized thermal plasma in the reaction chamber of the reactor.

19. A method according to claim 15, wherein the tail flame is directed vertically upwardly, with the quench probe extending vertically.

* * * * *